US006924124B1

(12) United States Patent
Singh

(10) Patent No.: US 6,924,124 B1
(45) Date of Patent: Aug. 2, 2005

(54) FEEDING STRATEGIES FOR CELL CULTURE

(75) Inventor: Pankaj Singh, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 10/227,154

(22) Filed: Aug. 23, 2002

(51) Int. Cl.[7] .......................... C12P 21/04; C12P 21/06
(52) U.S. Cl. .................. 435/70.1; 435/69.1; 435/71.1; 435/70.3
(58) Field of Search .............................. 435/69.1, 70.3, 435/253, 320.1, 252, 70.1, 71.1, 803, 325, 435/366, 404; 530/351, 410, 350; 514/12

(56) References Cited

U.S. PATENT DOCUMENTS

| | | | | |
|---|---|---|---|---|
| 4,931,543 A | * | 6/1990 | Halenbeck et al. | 530/351 |
| 5,407,810 A | * | 4/1995 | Builder et al. | 435/69.1 |
| 5,705,364 A | * | 1/1998 | Etcheverry et al. | 435/70.3 |
| 5,789,199 A | * | 8/1998 | Joly et al. | 435/69.1 |
| 6,103,529 A | * | 8/2000 | Price et al. | 435/404 |

OTHER PUBLICATIONS

Liu, Yung-Chuan, Cultivation of Recombinant *E. coli* to Achieve High Cell Density with High Level of Pnencilin G Acylase Activity., Dec. 9, 1999, Proc. Natl. Sci Coun. vol. 24, No. 4. 2000. pp. 156-160.* deZengotita et al., "Phosphate Feeding Improves High-Cell-Concentration NS0 Myeloma Culture Performance for Monoclonal Antibody Production,"*Biotechnology and Bioengineering* 69(5):566-576, 2000.

Jo et al., "Step-Fortifications of Nutrients in Mammalian Cell Culture,"*Biotechnology and Bioengineering* 42:1218-1228, 1993.

Sato et al, "Stimulation of monoclonal antibody production by human-human hybridoma cells with an elevated concentration of potassium or sodium phosphate in serum-free medium,"*Cytotechnology* 2:63-67, 1989.

* cited by examiner

*Primary Examiner*—Robert A. Wax
*Assistant Examiner*—Robert Mondesi
(74) *Attorney, Agent, or Firm*—Kathleen Fowler

(57) ABSTRACT

The invention is in the field of cell culture, particularly recombinant cell culture. More specifically, the invention relates to methods of fed batch CHO cell culture.

18 Claims, 2 Drawing Sheets

FEEDING STRATEGIES FOR CELL CULTURE

FIELD OF THE INVENTION

The invention is in the field of cell culture, particularly recombinant cell culture. More specifically, the invention relates to methods of fed batch CHO cell culture.

BACKGROUND

One goal of recombinant protein production is the optimization of culture conditions so as to obtain the greatest possible productivity. Even incremental increases in productivity can be economically significant.

CHO (Chinese hamster ovary) cell lines are often used for recombinant protein production because they grow well in either adherent or suspension culture, and efficiently produce many proteins. Further, CHO cells and recombinant proteins expressed in them have been extensively characterized and have been approved for use in clinical manufacturing by regulatory agencies.

Some of the methods to increase productivity in CHO cell culture include using enriched medium, monitoring and altering osmolarity during production, decreasing temperatures during specific phases of a cell culture, and/or the addition of sodium butyrate to induce expression during the production phase (see, for example, U.S. Pat. No. 5,705,364 to Etcheverry et al.). In addition, when CHO cells are grown in batch culture, periodic feeding of the cells with essential nutrients will also increase production (see, for example, U.S. Pat. No. 5,672,502 to Birch et al.).

However, there remains a need in the art to continually improve yields of recombinant protein from each cell culture run.

SUMMARY OF THE INVENTION

The invention relates to improved and optimized methods of producing recombinant proteins in CHO cells. In particular, the invention provides a method of producing a recombinant protein, the method comprising culturing a CHO cell culture genetically engineered to produce the protein in a tissue culture medium, and adding a feed solution to the cell culture, wherein the feed solution comprises an effective amount of a phosphate compound. Generally, it has been found that the phosphate should be added to achieve an increase in the final cell culture concentration of around 1 millimolar to about 10 millimolar phosphate. The phosphate compound can be selected from the group consisting of sodium phosphate, potassium phosphate, phosphoric acid, and other salts of phosphoric acid.

Optionally, the feed solution additionally comprises one or more amino acids. The invention finds particular use when the cells are under inducing conditions when the feed solution is added. The feed solution is added repeatedly, such as, for example, about every two days for 4 to 10 days. The methods of the invention result in increased production of the recombinant protein by the CHO cell culture as compared to the CHO cell culture in the absence of added feed solution. The methods of the invention are particularly useful for large scale culturing of CHO cell cultures.

DETAILED DESCRIPTION OF THE INVENTION

Figure 1:
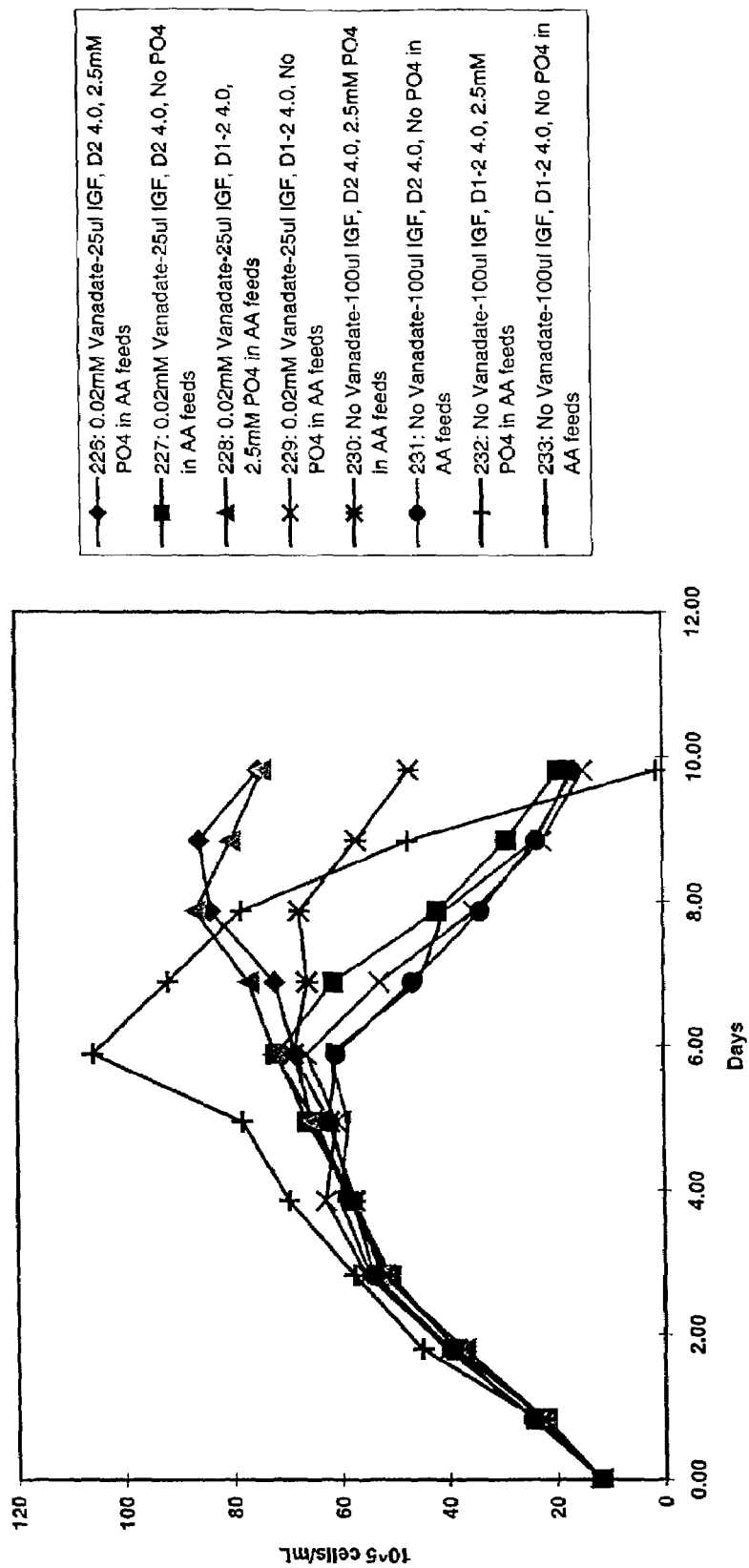
FIG. 1 is a graph of the viable cell density (VCD) over time for the following eight conditions: tank 226 was 0.02 mM Vanadate-25 ul IGF, D2 4.0, 2.5 mM PO4 in feeds (diamonds); tank 227 was 0.02 mM Vanadate-25 ul IGF, D2 4.0, No PO4 in feeds (squares); tank 228 was 0.02 mM Vanadate-25 ul IGF, D1-2 4.0, 2.5 mM PO4 (triangles); tank 229 was 0.02 mM Vanadate-25 ul IGF, D1-2 4.0, No PO4 in feeds (X's); tank 230 was No Vanadate-100 ul IGF, D2 4.0, 2.5 mM PO4 in feeds (stars); tank 231 was No Vanadate-100 ul IGF, D2 4.0, No PO4 in feeds (circles); tank 232 was No Vanadate-100 ul IGF, D1-2 4.0, 2.5 mM PO4 in feeds (crosses); tank 233 was No Vanadate-100 ul IGF, D1-2 4.0, No PO4 in feeds (narrow rectangles).

During CHO batch phase culture of recombinant cells, nutrients can become limiting, leading to a reduction in cell performance (as measured by cell viability, viable cell density, and recombinant protein production). To overcome these effects, batch cultures can be fed with a concentrated solution of medium and/or amino acids. This process is known as fed batch culture. During experiments with CHO fed batch culture, it was noticed that the acid used to buffer solutions for the feeds had an effect on performance of the cell culture. In particular, it was noticed that cultures fed amino acids buffered with phosphoric acid performed better than cultures fed amino acids buffered with hydrochloric acid. Additional experimentation determined that this effect was not due to the buffering action of the acid, but rather to the presence or absence of phosphate. Specifically, when CHO cultures were fed amino acids buffered with hydrochloric acid, with or without the addition of phosphate, the cultures receiving phosphate had enhanced performance.

Thus, the invention provides improved methods of producing recombinant proteins using batch culture in CHO cells. In particular, the invention provides a method of producing a recombinant protein, the method comprising culturing in batch culture in a tissue culture medium a CHO cell culture genetically engineered to produce the protein, and adding a feed solution to the cell culture, wherein the feed solution comprises an effective amount of a phosphate compound.

The amount and timing of addition of phosphate compound to the cell culture will vary slightly by cell line, and can be optimized by those skilled in the art. Generally, for most fed batch processes, it has been found that the phosphate compound should be added so as to achieve an increase in the cell culture concentration of around 0.1 millimolar to about 10 millimolar phosphate just after addition of the feed. Feed solutions can be added repeatedly. More frequent feeds will call for the addition of lower amounts of phosphate compound each time; conversely, less frequent feeds will call for the addition of higher amounts of phosphate compound. However, very high concentrations of phosphate in the cell culture should be avoided as such can be toxic to CHO cells. In illustrative embodiments described below, a feed solution containing a phosphate compound is added about every two days in an amount to result in a concentration of phosphate in the cell culture of about 1.5 to about 3.5 mM, preferably about 2.5 mM phosphate.

The phosphate compound can be added in any non-conjugated form that is not toxic to the cell. For example, the phosphate compound can be selected from the group consisting of sodium phosphate, potassium phosphate, phosphoric acid, and other salts of phosphoric acid. The phosphate compound can be added along with other nutrients in the feed. Other nutrients can include, but are not limited to, any combination of the following: L-Glutamine, L-Asparagine, L-Proline, L-Methionine, L-Isoleucine, L-Leucine, L-Phenylalanine, L-Tryptophan, L-Lysine, L-Histidine, L-Arginine, L-Serine, L-Glycine, L-Threonine, L-Valine, L-Cystine, L-Tyrosine, IGF-1, insulin, hydrocortisone, sodium bicarbonate, dichloroacetate, acids, bases, glucose, other carbohydrates, peptones, hydrosylates, and vitamins. For example, the feed can contain a concentrated medium solution with a phosphate compound, and/or various additions of amino acids with a phosphate compound. In a non-limiting, illustrative embodiment below, at least one of the feeds contain a concentrated solution of 17 amino acids. The feeds can be different in composition on different days, or the same. An effective amount of phosphate compound will result in increased production of the recombinant protein by the cell culture as compared to the CHO cell culture in the which has been fed a feed solution that does not contain the phosphate compound.

The proteins can be produced recombinantly in CHO (Chinese hamster ovary) cells and are preferably secreted by CHO cells adapted to grow in cell culture. Preferably, the host cells are homogenous CHO cell lines. Such host cells are available from a number of depositaries and laboratories, such as the ATCC. The dihydrofolate reductase (DHFR)-deficient mutant cell line (Urlaub et al., 1980, Proc Natl Acad Sci USA 77:4216–4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527–566). In addition, these cells are easy to manipulate as adherent or suspension cultures and exhibit relatively good genetic stability. In addition, new animal cell lines can be established using methods well known by those skilled in the art (e.g., by transformation, viral infection, and/or selection, etc.).

By in vitro cell culture is meant the growth and propagation of cells outside of a multicellular organism or tissue. Typically, in vitro cell culture is performed under sterile, controlled temperature and atmospheric conditions in tissue culture plates (e.g., 10 cm plates, 96 well plates, etc.), or other adherent culture (e.g., on microcarrier beads) or in suspension culture and/or in roller bottles. Cultures can be grown in shake flasks, small scale bioreactors, and/or large-scale bioreactors. A bioreactor is a device used to culture animal cells in which environmental conditions such as temperature, atmosphere, agitation, and/or pH can be monitored and adjusted. A number of companies (e.g., ABS Inc., Wilmington, Del.; Cell Trends, Inc., Middletown, Md.) as well as university and/or government-sponsored organizations (e.g., The Cell Culture Center, Minneapolis, Minn.) offer cell culture services on a contract basis.

Further, the methods and cell cultures of the invention (adherent or non-adherent and growing or growth arrested), can be small scale cultures, such as for example in 100 ml containers having about 30 ml of media, 250 ml containers having about 80 to 90 ml of media, 250 ml containers having about 150 to 200 ml of media. Alternatively, the cultures can be large scale such as for example 1000 ml containers having about 300 to 1000 ml of media, 3000 ml containers having about 500 to 3000 ml of media, 8000 ml containers having about 2000 to about 8000 ml of media, and 15000 ml containers having about 4000 ml to about 15000 ml of media. Both small scale and large scale culturing can be performed in bioreactors. In preferred embodiments, the size of the culture is at least about 100 liters, more preferably at least about 1000 liters, still more preferably at least about 5000 liters, even more preferably at least about 7000 liters.

Various tissue culture media, including serum-free and/or defined culture media, are commercially available for cell culture. Tissue culture medium is defined, for purposes of the invention, as a medium suitable for growth of animal cells, and preferably mammalian cells, in in vitro cell culture. Typically, tissue culture media contains a buffer, salts, energy source, amino acids, vitamins and trace essential elements. Any medium capable of supporting growth of the appropriate eukaryotic cell in culture can be used; as shown below by way of example, variations in a serum-free medium composition did not affect the superior results obtained when phosphate was fed to the cell culture. Tissue culture media suitable for use in the invention are commercially available from, e.g., ATCC (Manassas, Va.). For example, any one or combination of the following media can be used: RPMI-1640 Medium, Dulbecco's Modified Eagle's Medium, Minimum Essential Medium Eagle, F-12K Medium, Iscove's Modified Dulbecco's Medium. When defined medium that is serum-free and/or peptone-free is used, the medium is usually highly enriched for amino acids and trace elements (see, for example, U.S. Pat. No. 5,122,469 to Mather et al., and U.S. Pat. No. 5,633,162 to Keen et al.).

In the methods and compositions of the invention, cells can be grown in serum-free, protein-free, growth factor-free, and/or peptone-free media. The term "serum-free" as applied to media includes any mammalian cell culture medium that does not contain serum, such as fetal bovine serum. The term "insulin-free" as applied to media includes any medium to which no exogenous insulin has been added. By exogenous is meant, in this context, other than that produced by the culturing of the cells themselves. The term "IGF-1-free" as applied to media includes any medium to which no exogenous Insulin-like growth factor-1 (IGF-1) or analog (such as, for example, LongR$^3$-IGF-1, see below) has been added. The term "growth-factor free" as applied to media includes any medium to which no exogenous growth factor (e.g., insulin, IGF-1) has been added. The term "protein-free" as applied to media includes medium free from exogenously added protein, such as, for example, transferrin and the protein growth factors IGF-1 and insulin. Protein-free media may or may not have peptones. The term "peptone-free" as applied to media includes any medium to which no exogenous protein hydrolysates have been added such as, for example, animal and/or plant protein hydrolysates. Peptone-free media has the advantages of lower lot to lot variability and fewer filtration problems than media containing plant or animal hydrolysates. Chemically defined media are media in which every component is defined and obtained from a pure source, preferably a non-animal source.

Preferably, the medium used is serum-free, or essentially serum-free. By "essentially serum-free" is meant that less than about 2% serum is present, more preferably less than about 1% serum is present, still more preferably less than about 0.5% serum is present, yet still more preferably less than about 0.1% serum is present.

Batch culture is well known in the art, as are methods of fed batch culture (see U.S. Pat. No. 5,672,502). Cells are cultured in a fixed volume, and supplementary nutrients are added. The methods of the invention can be used in combination with other types of culture. For example, cell cultures can be serial subcultured in larger and larger volumes of culture medium to as to maintain the cells in exponential phase, and then converted to a batch culture system when a desired volume or cell density is achieved. Then, the batch cell culture can be fed using the methods of the invention. For example, a CHO cell culture can be grown and progressively transferred from a small scale culture to a large scale culture, and then seeded at a desired cell density into a batch cell culture. Once in the batch cell culture, the cells can be fed using the methods of the invention. CHO cells can be maintained in batch culture for as long as recombinant protein production occurs. Preferably, the batch culture is maintained in a production phase for about 2 to about 16 days, more preferably for about 6 to about 12 days.

Further, the methods of the invention can be used in combination with known or yet to be discovered methods of inducing the production of recombinant proteins. By "inducing conditions" is meant a technique to increase the relative production per cell of a desired recombinant protein. Often, other cell processes (such as growth and division) are inhibited so as to direct most of the cells' energy into recombinant protein production. Such techniques include cold temperature shift, and additions of chemicals such as sodium butyrate (as described in U.S. Pat. No. 5,705,364 to Etcheverry et al., incorporated herein by reference), DMSO, DMF, DMA, TNF-alpha, phorbol 12-myristate 13-acetate, PMA, propionate, forskolin, dibutyryl cAMP, 2-aminopurine, adenine, adenosine, okadaic acid, and combinations of any of these techniques, to name just a few examples, as well as any yet to be described and/or discovered induction techniques. Typically, a batch culture of cells at high density is induced to produce the recombinant protein.

The invention can be used in the culture of cells that produce just about any protein, especially recombinant proteins. Examples of useful expression vectors that can be used to produce proteins are disclosed in WO 01/27299, and the pDC409 vector described in McMahan et al., 1991, Embo J. 10:2821. A protein is generally understood to be a polypeptide of at least about 10 amino acids, more preferably at least about 25 amino acids, even more preferably at least about 75 amino acids, and most preferably at least about 100 amino acids.

Generally, the methods of the invention are useful for the production of recombinant proteins. Recombinant proteins are proteins produced by the process of genetic engineering. The term "genetic engineering" refers to a recombinant DNA or RNA method used to create a host cell that expresses a gene at elevated levels, at lowered levels, or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96(6):2758–63). Preferably, the proteins are expressed under the control of a heterologous control element such as, for example, a promoter that does not in nature direct the production of that protein. For example, the promoter can be a strong viral promoter (e.g., CMV, SV40) that directs the expression of a mammalian protein. The host cell may or may not normally produce the protein. For example, the host cell can be a CHO cell that has been genetically engineered to produce a human protein. Alternatively, the host cell can be a human cell that has been genetically engineered to produce increased levels of a human protein normally present only at very low levels (e.g., by replacing the endogenous promoter with a strong viral promoter).

Particularly preferred proteins for expression are protein-based therapeutics, also known as biologics. Preferably, the proteins are secreted as extracellular products. Proteins that can be produced using the invention include but are not limited to Flt3 ligand, CD40 ligand, erythropoeitin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-$\beta$, tumor necrosis factor, leukemia inhibitory factor, oncostatin-M, and various ligands for cell surface molecules Elk and Hek (such as the ligands for eph-related kinases, or LERKS). Descriptions of proteins that can be produced according to the invention may be found in, for example, *Human Cytokines: Handbook for Basic and Clinical Research*, Vol. II (Aggarwal and Gutterman, eds. Blackwell Sciences, Cambridge Mass., 1998); *Growth Factors: A Practical Approach* (McKay and Leigh, eds., Oxford University Press Inc., New York, 1993) and *The Cytokine Handbook* (AW Thompson, ed.; Academic Press, San Diego Calif.; 1991).

Production of the receptors for any of the aforementioned proteins can also be improved using the invention, including the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such proteins are described in U.S. Pat. No. 5,767,064, incorporated herein by reference in its entirety.

Other proteins that can be produced using the invention include cluster of differentiation antigens (referred to as CD proteins), for example, those disclosed in *Leukocyte Typing VI (Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Proteins that are enzymatically active can also be produced according to the instant invention. Examples include metalloproteinase-disintegrin family members, various kinases, glucocerebrosidase, alpha-galactosidase A, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be produced by applying the instant invention.

The inventive compositions and methods are also useful for production of other types of recombinant proteins, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934–938; Reichmann et al., 1988, Nature 332:323–327; Roberts et al., 1987, Nature 328:731–734; Verhoeyen et al., 1988, Science 239:1534–1536; Chaudhary et al., 1989, Nature 339:394–397). Recombinant cells producing fully human antibodies (such as are prepared using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. For example, the invention can be used in the production of human and/or humanized antibodies that immunospecifically recognize specific cellular targets, e.g., any of the aforementioned proteins, the human EGF receptor, the her-2/neu antigen, the CEA antigen, Prostate Specific Membrane Antigen (PSMA), CD5, CD11a, CD18, NGF, CD20, CD45, CD52, Ep-cam, other cancer cell surface molecules, TNF-alpha, TGF-b1, VEGF, other cytokines, alpha 4 beta 7 integrin, IgEs, viral proteins (for example, cytomegalovirus), etc., to name just a few.

Various fusion proteins can also be produced using the invention. A fusion protein is a protein, or domain or a protein (e.g. a soluble extracellular domain) fused to a heterologous protein or peptide. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Another fusion protein is a recombinant TNFR:Fc, also known as "entanercept." Entanercept is a dimer of two molecules of the extracellular portion of the p75 TNF alpha receptor, each molecule consisting of a 235 amino acid TNFR-derived polypeptide that is fused to a 232 amino acid Fc portion of human IgG1. In fact, any of the previously described molecules can be expressed as a fusion protein including but not limited to the extracellular domain of a cellular receptor molecule, an enzyme, a hormone, a cytokine, a portion of an immunoglobulin molecule, a zipper domain, and an epitope.

After culturing using the methods of the invention, the resulting expressed protein can then be collected. In addition the protein can purified, or partially purified, from such culture or component (e.g., from culture medium or cell extracts or bodily fluid) using known processes. By "partially purified" means that some fractionation procedure, or procedures, have been carried out, but that more polypeptide species (at least 10%) than the desired protein is present. By "purified" is meant that the protein is essentially homogeneous, i.e., less than 1% contaminating proteins are present. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above.

For example, the purification of the polypeptide can include an affinity column containing agents which will bind to the polypeptide; one or more column steps over such affinity resins as concanavalin A-agarose, HEPARIN-TOYOPEARL (chromatography medium) or Cibacrom blue 3GA SEPHAROSE (agarose beads); one or more steps involving elution; and/or immunoaffinity chromatography. The polypeptide can be expressed in a form that facilitates purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can be tagged with an epitope and subsequently purified by using a specific antibody directed to such epitope. One such epitope FLAG (epitope tag) is commercially available from Kodak (New Haven, Conn.). It is also possible to utilize an affinity column comprising a polypeptide-binding polypeptide, such as a monoclonal antibody to the recombinant protein, to affinity-purify expressed polypeptides. Other types of affinity purification steps can be a Protein A or a Protein G column, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The invention having been described, the following examples are offered by way of illustration, and not limitation.

EXAMPLE

Amino Acid Feeds

During batch fed culture for production of a recombinant TNFR:Fc protein, a concentrated solution of amino acids was added to CHO cells under production conditions. The amino acid feed is conveniently added in two different buffers—a high pH solution to solubilize most amino acids, and a low pH solution to solubilize cystine and tyrosine. It was noticed that performance of the cell culture seemed to be improved when the low pH solution was buffered with phosphoric acid instead of hydrochloric acid. Accordingly, additional experimentation was performed to investigate the effect of phosphate in the amino acid feeds.

EXAMPLE

Addition of Phosphate Improves CHO Cell Culture Performance

In this experiment, the effect of altering the following three conditions was examined during production of a recombinant TNFR:Fc protein from CHO cells. The conditions that were tested were the following:
1. No phosphate or 2.5 mM $KH_2PO_4$ in amino acid feeds on days 4, 6 and 8.
2. 100 ul IGF-1 or 25 uL IGF-1 with 20 uM vanadate in the media.
3. A single day 2 feed, or the day 2 feed split into two halves and fed on day 1 and day 2.

Materials and Methods

Eight 2 liter production tanks with a 1 liter working volume (Applikon, Foster City, Calif.) were setup to investigate the effect of each combination of the three variables. Cells were seeded at about 7×10E5 cells per mL of medium with the indicated concentrations of vanadate and IGF-1 (Long [R3] IGF-1; GroPep, Australia). Growth was arrested by addition of sodium butyrate to 0.25 mM and incubation at 31 degrees C. The day 2 feed was a 15 fold concentrated serum-free complete medium. The days 4, 6, and 8 amino acid feed was a solution of 17 essential amino acids added as a 56× low pH amino acid feed (containing amino acids solubilized in a low pH buffer) and a 560× high pH amino acid feed (containing amino acids cystine and tyrosine, at a pH of about 12). When phosphate was added with the feed, it was present in the low pH amino acid solution.

The culture was maintained for 10 days, and samples taken daily to assay percent viability, viable cell density, and recombinant protein titer.

Results

Figure 2:
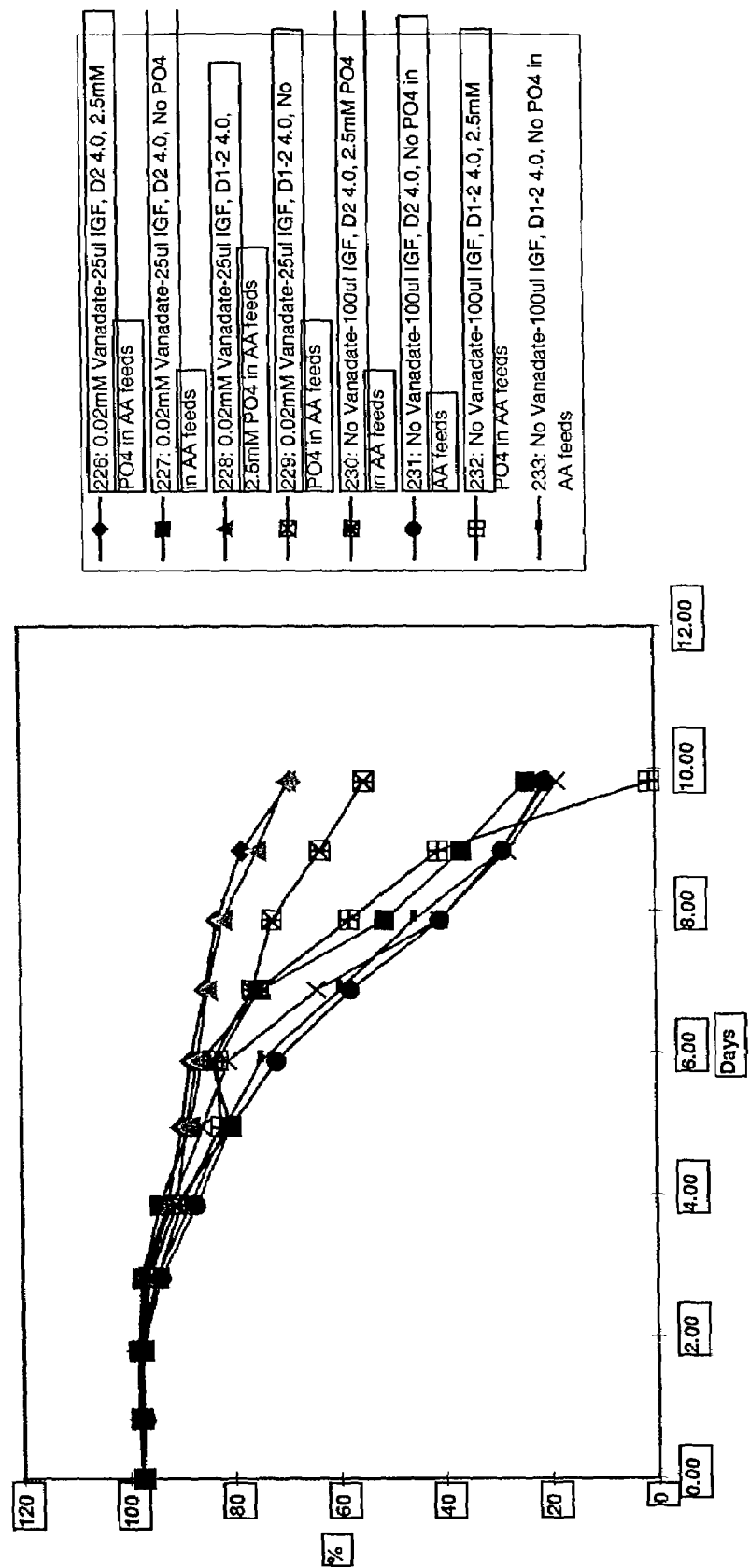
FIG. 2 is a graph of the percent viability over time, for each of the 8 different tanks. Conditions and symbols are the same as for the previous figure.

FIG. 1 is a graph of the viable cell density (VCD) over time, and FIG. 2 is a graph of the percent viability over time, for each of the 8 different tanks.

Although there was no significant difference in performance between the tanks that contained vanadate and those with no vanadate, addition of vanadate allowed a reduction in the amount of IGF-1 required. Reduction of IGF-1 in presence of vanadate is very desirable, as IGF-1 is a very expensive media component. No performance difference was observed between tanks with one day 2 feed and those with the split day 2 feed.

The effect of adding phosphate in the feeds was enormous. The cells in the tanks, which were fed with phosphate, grew to higher cell density than in the tanks without phosphate. Besides growing to higher cell density, viability also remained higher in the phosphate fed tanks. Furthermore, the resulting titers of TNFR:Fc protein were 65% higher in the phosphate fed tanks.

In conclusion, addition of phosphate in the feed sufficient to make the cell culture 2.5 mM phosphate immediately after addition caused a dramatic increase in recombinant protein production.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of producing a recombinant protein, the method comprising culturing a Chinese Hamster Ovary (CHO) cell culture genetically engineered to produce the protein in a tissue culture medium, and adding a feed solution to the cell culture, wherein the feed solution comprises a phosphate compound, where the phosphate compound is added in an amount sufficient to achieve a final cell culture concentration of from 1.5 millimolar to 3.5 millimolar phosphate, and wherein production of the recombinant protein by the cell culture is increased as compared to the CHO cell culture in the absence of the phosphate compound in the feed solution.

2. The method of claim 1, wherein the feed solution additionally comprises one or more amino acids.

3. The method of claim 1, wherein the phosphate compound is selected from the group consisting of sodium phosphate, potassium phosphate, phosphoric acid, and other salts of phosphoric acid.

4. The method of claim 2, wherein the phosphate compound is added as a component of an amino acid feed.

5. The method of claim 2, wherein the feed solution is added repeatedly.

6. The method of claim 5, wherein the feed solution is added about every two days.

7. The method of claim 1, wherein the cells are under inducing conditions when the feed solution is added.

8. The method of claim 7 wherein the inducing conditions comprise at least one condition selected from the group consisting of a reduction in temperature, an addition of a sodium butyrate solution, an addition of dimethylsulfoxide (DMSO), and an addition of dimethylformamide (DMF).

9. The method of claim 1, wherein the protein is a soluble form of a human tumor necrosis factor (TNF) receptor.

10. The method of claim 1, wherein size of the culture is at least about 100 liters.

11. The method of claim 10, wherein the size of the culture is at least about 1000 liters.

12. The method of claim 1, wherein the tissue culture medium is serum-free.

13. The method of claim 1, further comprising collecting the protein.

14. The method of claim 13, further comprising formulating the protein.

15. A method of producing a recombinant protein, the method comprising culturing a Chinese Hamster Ovary (CHO) cell culture genetically engineered to produce a protein in a tissue culture medium under induction conditions, and adding a feed solution to the cell culture, wherein the feed solution comprises an amount of a phosphate compound sufficient to bring the medium to about 2.5 mM phosphate after addition, and wherein production of the recombinant protein by the cell culture is increased as compared to the CHO cell culture in the absence of the phosphate compound in the feed solution.

16. The method of claim 15, further comprising adding one or more amino acids to the cell culture.

17. The method of claim 16, further comprising collecting the protein.

18. The method of claim 17, further comprising at least partially purifying the protein.

* * * * *